United States Patent [19]

Goldstein

[11] Patent Number: 5,366,869
[45] Date of Patent: Nov. 22, 1994

[54] MULTIPLE COAGULATION TEST DEVICE AND METHOD

[76] Inventor: Sheldon Goldstein, 30 S. Adelaid Ave., Penthouse K, Highland Park, N.J. 08904

[21] Appl. No.: 790,631

[22] Filed: Nov. 8, 1991

[51] Int. Cl.$^5$ .................. C12Q 1/56; C12Q 1/00; G01N 31/00; A61K 37/547
[52] U.S. Cl. .................. 435/13; 436/16; 424/94.64; 424/93.72; 424/530; 424/532; 514/2; 514/802; 514/834; 514/561; 514/21; 514/464; 514/12
[58] Field of Search .................. 424/93 A, 93 B, 93 C, 424/93 D, 93 E, 94.64, 93 W, 530, 532; 435/29, 13; 514/21, 2, 12, 464, 561, 802, 834; 436/16

[56] References Cited

U.S. PATENT DOCUMENTS

| | | | |
|---|---|---|---|
| 2,616,796 | 11/1952 | Schilling | 435/13 |
| 3,302,452 | 2/1967 | Leslie | 73/64.1 |
| 3,695,482 | 10/1972 | Mintz | 23/230 B |
| 3,836,333 | 9/1974 | Mintz | 23/259 |
| 3,918,908 | 11/1975 | Moyer et al. | 422/73 |
| 4,000,972 | 1/1977 | Braun et al. | 23/230 B |
| 4,074,971 | 2/1978 | Braun et al. | 23/230 B |
| 4,105,411 | 8/1978 | Biver | 23/253 R |
| 4,125,327 | 11/1978 | Margolis | 356/39 |
| 4,135,819 | 1/1979 | Schmid-Schönbein | 435/13 |
| 4,443,408 | 4/1984 | Mintz | 422/73 |
| 4,497,774 | 2/1985 | Scordato | 422/73 |
| 4,534,939 | 8/1985 | Smith et al. | 422/61 |
| 4,599,219 | 7/1986 | Cooper et al. | 422/61 |
| 4,640,896 | 2/1987 | Farrell et al. | 436/34 |
| 4,659,550 | 4/1987 | Schildknecht | 435/13 |
| 4,663,127 | 5/1987 | Jackson et al. | 422/58 |
| 4,671,939 | 6/1987 | Mintz | 422/58 |
| 4,752,449 | 6/1988 | Jackson et al. | 422/73 |
| 4,782,026 | 11/1988 | Baugh et al. | 436/69 |
| 4,865,984 | 9/1989 | Nemerson et al. | 435/288 |
| 4,871,677 | 10/1989 | Baugh et al. | 436/69 |
| 4,946,775 | 8/1990 | Yin | 435/13 |
| 5,302,348 | 4/1994 | Cusack et al. | 435/13 |

FOREIGN PATENT DOCUMENTS

| | | |
|---|---|---|
| 3540661 | 5/1987 | Germany . |
| 8910788 | 11/1989 | WIPO . |
| 9101383 | 2/1991 | WIPO . |
| 9116453 | 10/1991 | WIPO . |

Primary Examiner—Douglas W. Robinson
Assistant Examiner—K. Larson
Attorney, Agent, or Firm—McAulay Fisher Nissen Goldberg & Kiel

[57] ABSTRACT

A multiple coagulation test device has a plurality of tubes, each tube having associated coagulation detection means, and containing a treatment dosage of a coagulation enhancing agent. Whole blood samples are placed in the tubes which are mixed and warmed to 37° C., with the time to coagulation determined. The agent giving the lowest clotting time is selected as the most effective treatment for reducing hemorrhaging within a few minutes and the selected treatment begun. Utilizing the inventive device eliminates the need to use a multiple agent approach, by identifying the most effective course of action.

8 Claims, 1 Drawing Sheet

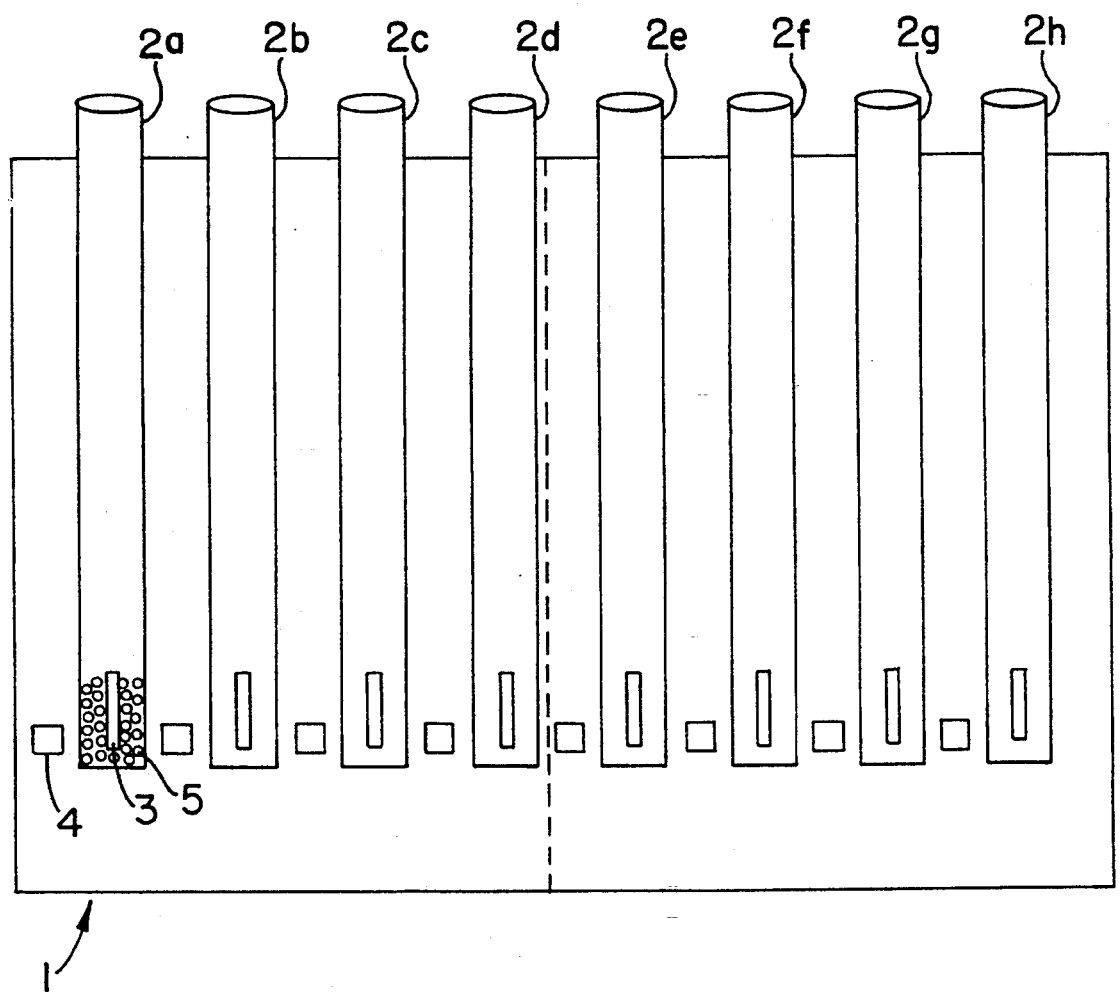

MULTIPLE COAGULATION TEST DEVICE AND METHOD

TECHNICAL FIELD

This invention relates to devices for use in quickly determining the causes and treatment for peri-operative or non-surgical hemorrhaging in a patient.

BACKGROUND

A heart-lung machine is typically used during heart surgery for coronary artery bypass, valvular replacement or proximal aortic reconstruction. Such a machine substitutes for the function of the heart muscle to pump blood throughout the body, and substitutes for lung function by removing carbon dioxide and adding oxygen to the patient's blood.

To use the heart-lung machine, full arrest of the coagulation cascade in the blood is required to prevent clot formation on the surfaces of the machine. In the coagulation cascade fibrin formation is initiated with the release from damaged cells of a complex protein known as tissue factor. This initiates the coagulation cascade which ultimately results in fibrin generation. The arrest of the cascade is accomplished typically by administering heparin to the patent. Heparin impedes coagulation by enhancing the effectiveness of anti-thrombin III, a naturally occurring inhibitor of coagulation. It does this by causing a conformational change that exposes additional binding sites on the anti-thrombin III molecule, which increases the ability of antithrombin III to bind with factors XIIa, XIa, IXa and Xa, which in turn accelerates their ability to inhibit the formation of fibrin. After the period of cardiopulmonary bypass is completed, the heparin effect is reversed by administering an antagonist agent, such as protamine.

Determining the proper number of units of heparin to be administered is not easily determined because of two phenomena. First, the amount of heparin that must be injected to achieve a certain plasma heparin concentration varies from patient to patient. Second, a given heparin level does not reflect an exact state of anticoagulation in a particular patient because of a number of factors peculiar to individual patients such as extravascular depots, hemodilution, hypothermia, heparin resistance and anti-thrombin III deficiency.

To determine whether the heparin administered has effectively reduced the ability of the blood to clot, the activated coagulation time (ACT) is measured. The ACT was introduced by Hattersley in 1966 and is a method for the rapid determination of the Lee-White whole blood clotting time. Although initially performed by manual rotation of a test tube and visual inspection for the presence of a clot, the test is typically performed via an automated method known as the HEMOCHRON (International Technidyne, Edison, N.J.). Typically, a sample containing two cc of whole blood is obtained and placed in an ACT tube and the time recorded. The tube is shaken to mix the blood with a diatomaceous powder which promotes coagulation by its high surface area. The tube is then warmed to 37° C. A magnetic rod placed in the tube is observed by a magnetic detector, and when coagulation occurs, the rod is displaced, signalling completion of the test. This test typically takes about $107 \pm 13$ seconds in a patient with normal coagulation status.

The ACT is currently first measured to provide a baseline ACT and then is measured again after administration of heparin to document whether a safe level of anticoagulation has been attained. The ACT is also measured serially during surgery, usually about every 30 minutes, to be sure that adequate anticoagulation is maintained in the face of metabolism changes and excretion of heparin.

The ACT is also used after surgery is completed. At this time, the heart has been restarted and is pumping blood through the lungs where oxygen is added to the blood and carbon dioxide is removed. The heparin anticoagulation effect is reversed by the administration of an antagonist to heparin, such as protamine. Protamine is polycationic and forms a complex with heparin, thus reversing its effects on Anti-Thrombin III. After administering protamine, the ACT is measured to determine if the protamine has adequately reversed the effects of heparin.

Sometimes, however, the administration of protamine does not return the ACT to the baseline (normal) condition and the patient may experience bleeding. Although many clinicians associate an increased ACT with a prolonged heparin effect, the ACT is limited in that it is a test of essentially the entire coagulation system, and as such, it is affected by other changes in the coagulation cascade. Therefore, an elevated ACT after heparin reversal with protamine does not necessarily indicate that residual heparin is the cause of the elevated ACT. In addition to residual heparin, destruction of serine protease (proteins required for blood to clot, otherwise known as clotting factors) hypofibrinogenemia, fibrinolysis and platelet abnormalities, both qualitative and quantitative, can influence the ACT. Decreased levels of fibronectin, a substance which is involved in platelet adhesion, may also result in increased bleeding.

One device currently used to assist in determining protamine dose is the HEPCON (HemoTec Inc., Englewood, Colo.). The HEPCON device consists of four chambers which contain specific amounts of protamine, thromboplastin and diluent. Air bubbles percolate through a blood sample in each chamber until a photocell detects clot formation in one of the chambers. Based upon the patient's height and weight, the device computes the heparin level. In essence, this device confirms whether or not a patient's bleeding tendency is due to heparin. If protamine administration is followed by obtaining an elevated ACT and a HEPCON test produces a reading of zero, this indicates that no heparin is circulating and it is likely that one or more other etiologies may be responsible for the hemorrhaging.

Bleeding in general surgical or non-surgical patients, including those involved in cardiopulmonary bypass surgery where there is no longer any circulating heparin, could be due to a decreased level of coagulation factors such as factors V, VIII, XIII and fibrinogen, as well as thrombocytopenia, or more commonly, abnormal platelet function, decreased levels of fibronectin, complement activation and fibrinolysis. Decreased levels of serine proteases and platelets could be due to low grade coagulation during bypass with consumption of the factors and platelets, or more likely, damage and destruction sustained when exposed to the surface of the oxygenator.

The anesthesiologist and surgeon are often faced with the situation that a patient is bleeding significantly and it is not due to heparin. A similar situation may occur in patients with massive bleeding due to a medical etiology. Because of the numerous possibilities of which factor or combination of factors is needed to stem the hemorrhaging, combined with the extremely limited amount of time available, the patient is frequently treated with a shotgun therapy, for example, by administration of platelets, fresh frozen plasma, desmopressin acetate (DDAVP) and sometimes epsilo-amino caproic acid (AMICAR) and cryoprecipitate. Since the use of platelets, fresh frozen plasma and cryoprecipitate all carry the risk of disease transmission, a system to rapidly determine if one or two therapies would be sufficient would decrease the risk to the patient of contracting hepatitis, AIDS, and numerous other diseases. Furthermore, in cases where it is determined that DDAVP or AMICAR would be therapeutic, the patient would be spared transfusion of blood products altogether. An additional reason to rapidly determine the specific appropriate therapy is that as long as there is a deficiency in blood coagulation, the patient will require transfusion of packed red blood cells (PRBCs). In addition to the risk of disease transmission, transfusion of large amounts of PRBCs dilutes the coagulation factors and platelets in the blood, resulting in a "dilutional coagulopathy", thus possibly worsening the degree of hemorrhaging.

At present, complete, definitive coagulation studies can only be done in the laboratory, which takes too long to be of use in determining a specific therapy against massive hemorrhage associated with an elevated ACT, whether under operating room or non-operating room conditions. -There is a need for a method that is rapid enough to allow a doctor to determine and administer a specific therapy under the severe time constraints posed by an episode of rapid massive bleeding whether in the operating room or otherwise.

SUMMARY OF THE INVENTION

It is an object of the present invention to provide a device which provides specific indications of the particular factors or substances which will positively influence the coagulation effectiveness of whole blood.

It is a further object to provide a device which can be used rapidly yet is sufficiently specific to identify particular factors or substances which can be used to treat intra-operative, post-operative or non-surgical bleeding.

According to the present invention, a clot detection device comprises a plurality of tubes, each of which contains a comparable dosage of a patient's blood. Each tube is contacted with a particular treatment alternative individually. For example, one tube may have an anti-heparin agent such as protamine, or will have fresh frozen plasma or platelets or amicar. The standard ACT test, or other clot detection system will then be carried out, i.e. each tube will include clot detecting means such as a magnetic rod with an associated detector and will be shaken and have their temperature elevated and the effects on coagulation will be assessed. Depending on the most effective treatment for increasing the coagulation effect, a suitable treatment will be determined and applied. Typically, the ACT test takes approximately two minutes and can be done in an operating room without utilizing a separate laboratory facility. Of course, a photocell detector or other detecting means may be used so long as the endpoint is the detection of a fibrin clot in a timed manner.

Utilizing the present invention, a device is provided for immediate operating room or non-operating room use which produces results indicating a proper course of treatment without resort to a shotgun approach which requires an addition of six or more agents to a patient and thus avoids several of the complications inherent in utilizing such an approach. The device thus allows rapid determination of a specific treatment in a hemorrhaging situation without awaiting laboratory test results.

BRIEF DESCRIPTION OF THE DRAWINGS

The FIGURE shows one embodiment of the device of the present invention for preforming a multiple coagulation time test.

DETAILED DESCRIPTION OF THE INVENTION

Referring to the figure, a device according to the invention is shown. The device 1 has 8 tubes 2A-H, each tube containing a magnetic rod 3 and having an associated magnetic detector 4. Each tube additionally contains a diatomaceous powder and an individual or combination of agent 5 for promoting coagulation.

The tubes are preferably sized to accept a 2.5 cc sample of whole blood. To each tube is added a different therapy for coagulation disorders, based upon a standard dose for a 70 kg adult with a blood volume of 5,000 co. The dose is then divided by 2000 to obtain a dose to be added to each tube.

Tube 2A is a standard and will contain the blood without treatment but after protamine has been administered to the patient. Tube 2B has 25 ucg of protamine. Tube 2C has 0.5 cc of fresh frozen plasma (based upon a dose of 4 units of fresh frozen plasma). Tube 2D has 0.25 cc of platelets, based upon a dose of 10 units of platelets. Tube 2E has 0.1 cc of cryoprecipitate, based upon a dose of 10 units. Tube 2F has 2.5 mg of Amicar, based on a loading dose of 5 grams. Tube 2G has 0.2 cc of desmopressin acetate, based upon a total dose of 0.3 mg/kg. Tube 2H contains 0.14 mg/kg of aprotinin. Each tube has 15 mg of diatomaceous earth.

These doses are based on a whole blood sample of 2.5 cc. However, the device may be designed to use the smallest volume of whole blood which still offers accurate test results, for example, a sample size ranging from 0.5 to 2.5 cc could be used. Of course, larger samples may also be used The initial time is noted when the blood is added to the tubes, which are mixed and heated to 37° C. Preferably, this is done simultaneously. The magnetic detectors then indicate when coagulation occurs and the times are noted.

In operation, if a patient's ACT after protamine administration remains elevated, the HEPCON is zero, and there is bleeding, the inventive device would be used and a therapy chosen based on the first treatment which brought the ACT closest to its baseline value. If bleeding continues, the treatment which was the next most effective would be administered, etc.

The number of tubes and treatments may be varied considerably. For example, each tube may contain a blood clotting agent such as coagulation factors I (fibrinogen), II (prothrombin), IIa (thrombin), III (thromboplastin), IV, V, VI, VII, VIII, IX, X, XI, XII, recombinant coagulation factors, bovine coagulation factors, coagulation factor VIII:C, Von Willebrand factor, platelets, fibronectin, thrombin, plasminogen, plasminogen activator, plasmin, desmopressin acetate (DDAVP), epsilo-amino caproic acid (amicar), cryoprecipitate, fresh frozen plasma, protamine, aprotinin and mixtures thereof.

Preferably, 6–10 tubes are incorporated in the device and the individual stop times noted and/or recorded automatically, utilizing suitable instrument control apparatus. Of course, more of less tubes may be used as necessary, as determined in light of experience and most likely or least invasive courses of action. For example, one tube may include both amicar and desmopressin acetate since neither carries the risk of disease transmission.

It is also contemplated that tube pack containing 3–5 tubes each prefilled with specific treatment agents would be supplied to the user and combined with other packs if needed. Bases on experience, severity of hemorrhaging, etc, a user could select the appropriate pack(s) for a first run in the device and supplement the choice as needed.

Utilizing the inventive device, results are given within about 2 minutes in an operating or emergency room setting, with the results communicated immediately to the attending personnel. Treatment can be given immediately and selectively targeted to give the most effective results. In many cases, risk of disease transmission is reduced as shotgun therapy is avoided.

I claim:

1. A method for determining the treatment required to arrest hemorrhaging in a patient comprising
   a) providing a series of different agents capable of enhancing blood clotting;
   b) obtaining a series of samples of the patient's blood;
   c) mixing a sample of blood with each of the individual agents to prepare a series of mixtures, each mixture of said series containing a different agent;
   d) simultaneously measuring the clotting time for each mixture in said series; and
   e) selecting the agent in said series which produces the most rapid clotting time.

2. The method of claim 1 wherein the blood clotting enhancing agent is selected from the group consisting of coagulation factors, platelets, plasminogen activator, desmopressin acetate (DDAVP), epsilo-amino caproic acid, protamine, aprotinin, fibronectin, thrombin, plasminogen, plasma, a cryoprecipitated plasma product and prostacyclin.

3. The method of claim 2 wherein the coagulation factor is coagulation factor I (fibrinogen), Ia (fibrin), II (prothrombin), IIa (thrombin), III (thromboplastin), IV, V, VI, VII, VIII, IX, X, XI, XII, VIII:C, von Willebrand factor or a bovine coagulation factor.

4. The method of claim 2 wherein the plasma is bovine plasma, or human fresh frozen plasma.

5. A method for arresting hemorrhaging in a patient comprising
   a) providing a series of different agents capable of enhancing blood clotting;
   b) obtaining a series of samples of the patient's blood;
   c) mixing a sample of blood with each of the individual agents to prepare a series of mixtures, each mixture of said series containing a different agent;
   d) simultaneously measuring the clotting time for each mixture in said series;
   e) selecting the agent in said series which produces the most rapid clotting time; and
   f) administering a blood clotting effective amount of the selected agent from step e) to the patient.

6. The method of claim 5 wherein the blood clotting enhancing agent is selected from the group consisting of coagulation factors, platelets, plasminogen activator, desmopressin acetate (DDAVP), epsilo-amino caproic acid, protamine, aprotinin, fibronectin, thrombin, plasminogen, plasma, a cryoprecipitated plasma product and prostacyclin.

7. The method of claim 6 wherein the coagulation factor is coagulation factor I (fibrinogen), Ia (fibrin), II (prothrombin), IIa (thrombin), III (thromboplastin) IV, V, VI, VII, VIII, IX, X, XI, XII, VIII:C, von Willebrand factor or a bovine coagulation factor.

8. The method of claim 6 wherein the plasma is bovine fresh frozen plasma, or human plasma.

* * * * *